US007842045B2

(12) United States Patent
Vandenbroek

(10) Patent No.: US 7,842,045 B2
(45) Date of Patent: Nov. 30, 2010

(54) SINGLE FIRE VASCULAR CLIP APPLIER WITH DISPOSABLE JAW

(75) Inventor: Frans Vandenbroek, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 988 days.

(21) Appl. No.: 11/039,188

(22) Filed: Jan. 19, 2005

(65) Prior Publication Data
US 2006/0161182 A1 Jul. 20, 2006

(51) Int. Cl.
*A61B 17/10* (2006.01)
*A61B 17/00* (2006.01)
(52) U.S. Cl. .................. 606/142; 606/206; 606/207
(58) Field of Classification Search ........... 606/139, 606/142, 205, 206, 207, 208; 30/131, 132, 30/194, 222–262, 173, 175; 81/385, 417–419, 81/421–424, 321, 305, 306, 427
See application file for complete search history.

(56) References Cited

U.S. PATENT DOCUMENTS

| 770,347 | A | * | 9/1904 | Brown | ............ | 30/253 |
|---|---|---|---|---|---|---|
| 1,612,606 | A | * | 12/1926 | Carlson | ............ | 30/248 |
| 1,869,295 | A | * | 7/1932 | Atterbury | ............ | 30/248 |
| 2,108,325 | A | * | 2/1938 | Ziegler | ............ | 606/120 |
| 3,040,420 | A | * | 6/1962 | Kulp | ............ | 29/229 |
| 3,252,221 | A | * | 5/1966 | Roberts et al. | ............ | 433/40 |
| 3,266,494 | A | | 8/1966 | Brownrigg et al. | | |
| 3,326,216 | A | * | 6/1967 | Wood | ............ | 606/158 |
| 3,336,666 | A | * | 8/1967 | Calkin | ............ | 30/90.1 |
| 3,422,532 | A | * | 1/1969 | Ballard | ............ | 30/252 |
| 3,827,277 | A | | 8/1974 | Weston | | |
| 3,882,854 | A | | 5/1975 | Hulka et al. | | |
| 3,999,555 | A | | 12/1976 | Person | | |
| 4,043,343 | A | | 8/1977 | Williams | | |

(Continued)

FOREIGN PATENT DOCUMENTS

DE  214727  10/1909

(Continued)

OTHER PUBLICATIONS

Davis and Geck Brochure "Introducing Multiclip (R) Disposable Ligating Clip Device", Journal of T+CS, vol. 86-No. 6, Dec.1983 (cover sheet only-no further information available.

(Continued)

*Primary Examiner*—Tan-Uyen (Jackie) T Ho
*Assistant Examiner*—Dianne Dornbusch
(74) *Attorney, Agent, or Firm*—John F. Heal; Cynthia A. Bonner; David G. Majdali

(57) ABSTRACT

A single-fire clip applier with disposable jaws and re-usable handles is provided. The first jaw member is coupled to a second jaw member by a connector spring. The connector spring biases the jaws to an open at rest position. The jaws are releasably mountable to a post on the handles. Actuation of the handles produces a corresponding actuation of the jaws. After use, the jaws may be disposed and the handles re-sterilized. Different sized jaws for different sized clips may be used with one common re-usable handle.

16 Claims, 6 Drawing Sheets

U.S. PATENT DOCUMENTS

| | | | |
|---|---|---|---|
| 4,064,881 A | | 12/1977 | Meredith |
| 4,112,951 A | | 9/1978 | Hulka et al. |
| 4,169,476 A | | 10/1979 | Hiltebrandt |
| 4,187,712 A | | 2/1980 | Samuels et al. |
| 4,228,895 A | | 10/1980 | Larkin |
| 4,296,751 A | * | 10/1981 | Blake et al. .................. 606/143 |
| 4,423,729 A | | 1/1984 | Gray |
| 4,589,631 A | * | 5/1986 | Markus ........................ 254/28 |
| 4,648,401 A | | 3/1987 | Mattson |
| 4,896,661 A | | 1/1990 | Bogert et al. |
| 4,936,447 A | | 6/1990 | Peiffer |
| 5,052,402 A | | 10/1991 | Bencini et al. |
| 5,133,727 A | | 7/1992 | Bales et al. |
| 5,152,778 A | | 10/1992 | Bales, Jr. et al. |
| 5,163,945 A | | 11/1992 | Ortiz et al. |
| 5,215,101 A | | 6/1993 | Jacobs et al. |
| 5,234,460 A | | 8/1993 | Stouder, Jr. |
| 5,261,918 A | | 11/1993 | Phillips et al. |
| 5,263,967 A | | 11/1993 | Lyons, III et al. |
| 5,297,538 A | | 3/1994 | Daniel |
| 5,304,183 A | | 4/1994 | Gourlay et al. |
| 5,304,203 A | | 4/1994 | El-Mallawany et al. |
| 5,331,739 A | * | 7/1994 | Basangy ........................ 30/28 |
| 5,354,304 A | | 10/1994 | Allen et al. |
| 5,368,606 A | | 11/1994 | Marlow et al. |
| 5,380,338 A | | 1/1995 | Christian |
| 5,391,166 A | | 2/1995 | Eggers |
| 5,472,439 A | | 12/1995 | Hurd |
| 5,529,571 A | | 6/1996 | Daniel |
| 5,582,084 A | | 12/1996 | Sarmiento |
| 5,591,182 A | | 1/1997 | Johnson |
| 5,662,667 A | | 9/1997 | Knodel |
| 5,697,889 A | | 12/1997 | Slotman et al. |
| 5,735,005 A | * | 4/1998 | Wang ............................ 7/127 |
| 5,735,873 A | | 4/1998 | MacLean |
| 5,749,893 A | | 5/1998 | Vidal et al. |
| 5,810,865 A | | 9/1998 | Koscher et al. |
| 5,814,069 A | | 9/1998 | Schulze et al. |
| 5,867,877 A | * | 2/1999 | Patterson et al. ........... 24/598.5 |
| 5,893,875 A | | 4/1999 | O'Connor et al. |
| 5,921,996 A | | 7/1999 | Sherman |
| 5,925,052 A | | 7/1999 | Simmons |
| 5,925,064 A | | 7/1999 | Meyers et al. |
| 5,972,003 A | | 10/1999 | Rousseau |
| 5,984,934 A | | 11/1999 | Ashby et al. |
| 6,077,290 A | | 6/2000 | Marini |
| 6,108,845 A | * | 8/2000 | Hung et al. .................... 7/128 |
| 6,159,223 A | | 12/2000 | Danks et al. |
| 6,282,995 B1 | * | 9/2001 | Lin ............................ 81/423 |
| 6,647,835 B1 | * | 11/2003 | Tseng ......................... 81/423 |
| 6,725,748 B1 | * | 4/2004 | Tseng ......................... 81/418 |
| 6,733,514 B2 | * | 5/2004 | Miser ......................... 606/206 |
| 7,216,523 B2 | * | 5/2007 | Frenken ....................... 72/416 |
| 7,322,995 B2 | * | 1/2008 | Buckman et al. ........... 606/157 |
| 2002/0042620 A1 | | 4/2002 | Julian et al. |
| 2002/0053262 A1 | * | 5/2002 | Chang ......................... 81/302 |
| 2006/0027056 A1 | * | 2/2006 | Hsien ......................... 81/427 |
| 2006/0032344 A1 | * | 2/2006 | Hernandez, Jr. ............ 81/427.5 |

FOREIGN PATENT DOCUMENTS

| | | |
|---|---|---|
| DE | 4100219 A | 7/1992 |
| WO | WO00/42922 | 7/2000 |

OTHER PUBLICATIONS

Vitalitec International Brochure, SLS-Clip Set Loading System (four pages from brochure attached, no further information available).

Weck Closure Systems (TM) Ligating Clips brochure (four pages from brochure attached, no further information available).

International Searching Authority, International Search Report and Written Opinion for PCT/ US2005/045503, dated Apr. 20, 2006.

Co-Pending U.S. Appl. No. 11/021,852, filed Dec. 23, 2004 Title: Surgical Instrument With Improved Handle Assembly.

Co-Pending U.S. Appl. No. 10/381,970, filed Mar. 5, 2004 Title: Multiple Clip Applier Apparatus and Method.

Co-Pending U.S. Appl. No. 11/536,467, filed Sep. 28, 2006. Title: Manually Actuated Surgical Clip Applier.

Co-Pending U.S. Appl. No. 10/518,436, filed Dec. 16, 2004. Title: Clip Applier Cartridge With Internal Ratchet.

Co-Pending U.S. Appl. No. 10/815,149, filed Mar. 30, 2004 Title: Convertible Surgical Clip Applier System.

* cited by examiner

SINGLE FIRE VASCULAR CLIP APPLIER WITH DISPOSABLE JAW

BACKGROUND

This invention relates generally to surgical clip appliers and, in particular, single fire clip appliers with disposable jaws and methods thereof.

Various types of surgical instruments have been developed, including clip appliers, for the occlusion and ligation of vessels as well as other conduits and tissue structures. Clip appliers typically include a handle connected to a pair of clip compressing jaw members. In one configuration, the jaw members are movable with respect to each other when a user, e.g., a surgeon, operates the handle. A surgical clip is first retrieved from a clip dispenser and loaded in between the jaw members. A loaded surgical clip is placed over or around a desired section of tissue, vessel, another clip or another similar object. The clip is compressed as the jaw members move toward each other thereby applying the clip.

To save costs, single fire clip appliers are typically made re-usable and thus are re-sterilized for future use. The clip appliers, however, may not be robust enough to withstand repeated sterilization. For example, during repeated autoclave cycles the clip applier and, in particular, the jaws may be damaged. Batch processing specifically can trigger collisions with other instruments, which can bend or misalign the jaws. Misaligned or otherwise damaged jaws may introduce or cause difficulties in clip applying operations, e.g., retrieving of a clip from a clip dispenser, or lead to dropping of clips or unsuccessful clip application onto the desired section of tissue, vessel, another clip or another similar object. Such damaged clip appliers can be returned to the manufacturer for repair, however, the loss-of-use of the instrument together with the shipping expense involved, unnecessarily increases the cost of the clip applier and ultimately each procedure.

SUMMARY

The present invention, in various embodiments, provides a single-fire clip applier having a re-usable handle and disposable jaws. In one embodiment, a surgical instrument for applying a surgical clip comprises a disposable first and second jaw member and a connector spring. In one aspect, the first disposable jaw member has a proximal end, a distal end, and a first raised platform with a first slot extending lengthwise along the first raised platform, the disposable second jaw member has a proximal end, a distal end, and a second raised platform with a second slot extending lengthwise along the second raised platform and the connector spring is releasably mounted to the first and second raised platform and has a first leg and a second leg. The first leg is slidably coupled to the slot of the first raised platform and the second leg is slidably coupled to the slot of the second raised platform with the connector spring biasing the proximal end of the first and second jaw members together and the distal end of the first and second jaw members apart, in one embodiment.

In another embodiment, a surgical instrument for applying a surgical clip comprises a disposable first jaw member having a distal end, a proximal end, and a first receiving means (e.g., platform and/or slots) positioned at the proximal end of the first jaw member and a disposable second jaw member having a proximal end, a distal end, and a second receiving means (e.g., platform and/or slots) positioned at the proximal end of the second jaw member and means for releasably connecting (e.g., connector spring) the first and second jaw members together through engagement of the first and second receiving means and biasing the proximal end of the first and second jaw members together and the distal end of the first and second jaw members apart.

In yet another embodiment, a method of applying a surgical clip in a patient during a surgical procedure using a surgical instrument is provided. The surgical instrument comprises a first and second disposable jaw member and a connector spring releasably mounted to the first and second jaw members. The jaw members, in one aspect, are releasably mounted to first and second handles and the method comprises joining distal ends of the first and second jaw members together, sliding the first and second jaw members on the first handle, engaging the first and second jaw members with a projection from the first handle, placing a clip between the distal ends of the first and second jaw members, closing the first and second jaw members and the clip, and releasing the clip from the first and second jaw members.

Many of the attendant features of the present invention will be more readily appreciated as the same becomes better understood by reference to the following detailed description and considered in connection with the accompanying drawings in which like reference symbols designate like parts throughout.

DETAILED DESCRIPTION

Figure 1:
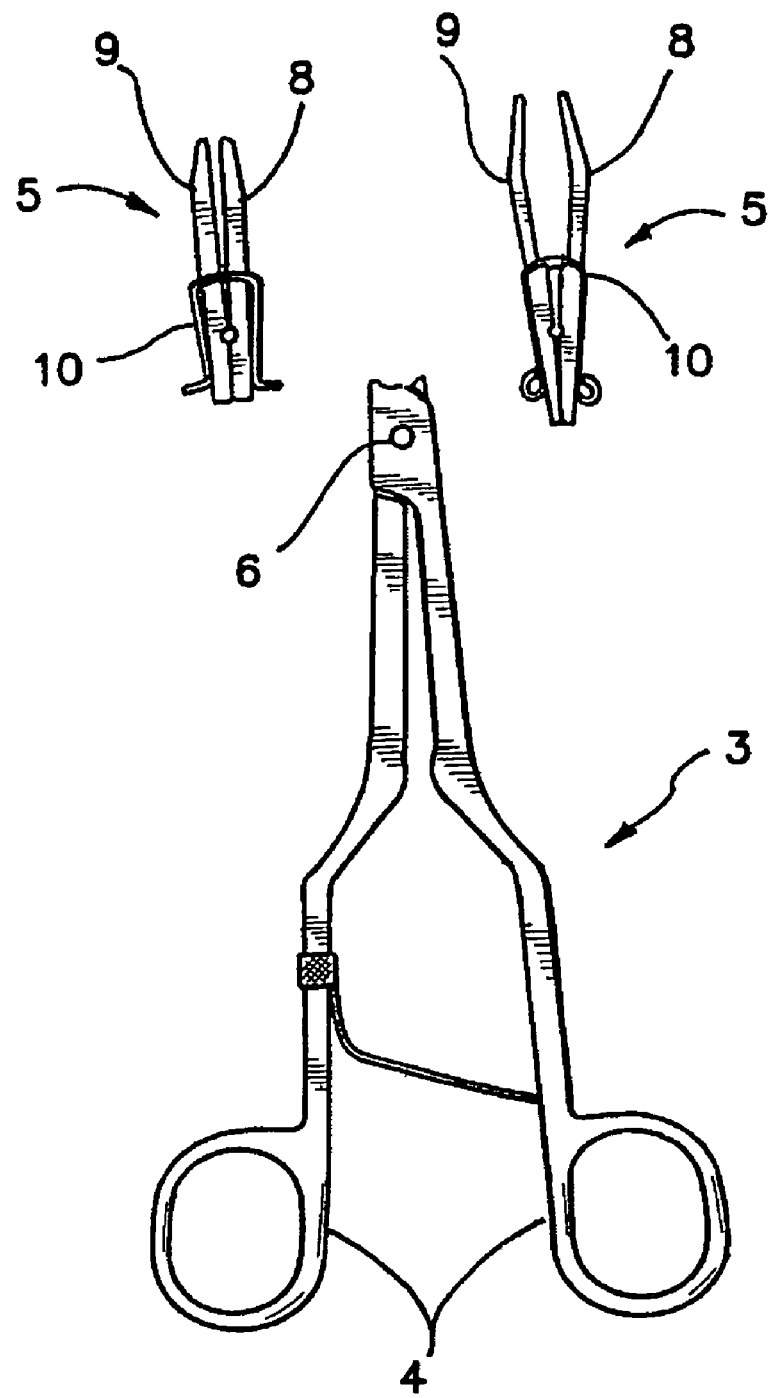
FIG. 1 illustrates a top-view of embodiments of the present invention with of a clip applier handle and two disposable jaws.
Figure 2:
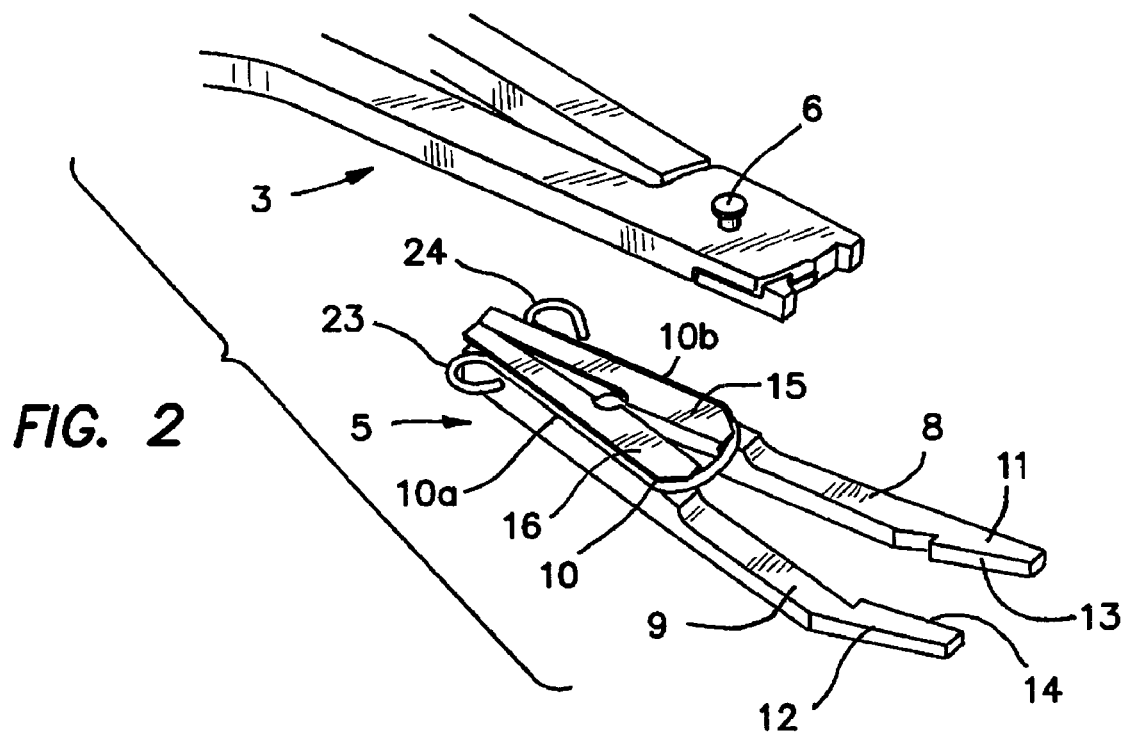
FIG. 2 illustrates a perspective view of one embodiment of the present invention of a clip applier handle and a disposable jaw.

In FIGS. 1-2, a set of re-usable clip applier handles 3 onto which a set of disposable jaws 5 may be attached prior to every procedure is shown. The jaws 5 are releasably mountable to the handles 3 on a post 6 extending from a point in which the ends of the jaws intersect. The post 6 also provides a pivotable connection for the handles 3. Finger loops 4 extend from one end, i.e., on the opposite end on which the jaws 5 may be attached, of each of the pair of re-usable handles 3. The jaws 5, in one embodiment, are configured such that one set of jaws, e.g., jaws 5a, are sized to receive small clips, e.g., about 5 mm clips, and another set of jaws, e.g., jaws 5b, are sized to receive large clips, e.g., about 10 mm clips. Also, post-procedure, the jaws may be detached from the handle and discarded. Thus, the fragile and usable part of the clip applier, the jaws, may be disposed, replaced and not exposed to repeated autoclave cycles. Thus, replaceable/disposable jaws ensure that a new jaw is used for each procedure and thereby clip retrieval and application are not hampered by jaws that may have been misaligned, deformed or damaged due to sterilization or re-use.

Additionally, the handles are re-usable and versatile to accommodate different sized jaws for utilizing different sized clips for various applications. The handles are also less fragile than the jaws or sufficiently robust to tolerate repeated re-sterilizations. As such, with the handles being re-usable and the jaws being disposable/replaceable the overall cost of the clip applier can be reduced and the benefits of being disposable or re-usable uncompromised.

The jaws 5 include a first jaw member 8 and a second jaw member 9 held together by a connector spring 10. Each jaw member 8, 9, in one embodiment, has a clip receiver or retention portion 11 and 12, respectively, for retrieving or crimping a clip, for example. A surgical clip, in one aspect of the present invention, is generally U-shaped or V-shaped with a pair of outwardly extending and generally opposed legs connected at an apex and twelve to twenty-four clips are stored in a dispenser. In one aspect, each clip retention portion 11 and 12 has a corresponding slot or groove 13 and 14 that increases retrieving, gripping or holding of a clip between the jaw members 8 and 9. In one embodiment, the clip retention portions 11 and 12 laterally extend towards and are generally parallel to each other as the jaw members brought together or closed. This generally parallel orientation enhances crimping of a clip disposed therebetween to fully compress a clip along its longitudinal axis.

Each jaw member 8, 9, in one embodiment, also has a raised connection portion or platform 15 and 16 releasably engaging the post 6 from the handles 3 and the connector spring 10. In one embodiment, the raised platforms 15, 16 are respectively integrated or monolithically formed with the jaw members 8, 9. In another embodiment, the raised platforms 15, 16 are separate or individual components in which the jaw members extend distally thereof or the raised platforms extend proximally from the respective jaw members. For example, in one aspect, the raised platforms sit on of the respective jaw members and extend longitudinally from about a midpoint of the jaw members to the proximal end of the jaw members.

The connector spring 10, in one aspect, is generally u-shaped in which the legs of the spring contact and extend along the sides of the raised connection portion 15 and 16. In one embodiment, each raised connection portion 15 and 16 has a corresponding slot or groove 17 and 18 that facilitate the slidable attachment of connector spring 10, e.g., legs 10a, 10b, to the jaw members 8 and 9 (See FIG. 7A-7B). The slots 17, 18, in one aspect, extend lengthwise or longitudinally along the respective platforms 15, 16. In one embodiment, one end of each raised connection portion 15 and 16 is tapered or otherwise curved or shaped to conform to the bight, bend or apex of the connector spring 10. The apex or curved/bent portion of the connector spring 10 extends between the jaw members 8 and 9 causing the jaw members to be coupled to each other and, in one embodiment, engages slots 17 and 18 increasing vertical alignment and stability of the jaw 5. In one embodiment, the slots 17, 18 extend further generally laterally along the distal end of the respective raised platforms 15, 16. As such, the slots 17, 18 may be tapered or otherwise curved or shaped to conform to the bight, bend or apex of the connector spring 10. The connector spring 10 being resilient or having resilient properties also biases the jaw members 8 and 9 to an open at rest position, i.e., the clip retention portions 11 and 12 or distal ends of the jaw members, are spread or moved away from each other. The opposite or proximal ends of each jaw member 8 and 9 are likewise biased toward each other by connector spring 10. In one aspect, the proximal ends of each jaw member 8 and 9 are slightly tapered and as such are sized smaller than the clip retention portions 11 and 12 or distal ends of the jaw members 8 and 9. In one aspect, the distal end of each jaw member or jaw tip is curved or otherwise atraumatic. In another aspect the jaw tips have inward protruding lips facilitating retrieval/retention of the clip.

In one embodiment, each raised connection portion or platform 15 and 16 includes a corresponding channel 19 and 20 extending from near the proximal end of each respective platform 15 and 16 or jaw member 8 and 9, e.g., where the jaw members and platforms are integrated or the proximal ends of the jaw members and the platforms generally correspond to each other or are generally located or adjacent to each other. Each channel 19 and 20 extends or angles along one side of each jaw member 8 and 9 and terminates at a generally semi-hemispherical space or opening 21 and 22. In one aspect, the proximal end of the channels 19, 20 are tapered. When brought together, the semi-hemispherical openings 21, 22 receive or generally define an enclosure for capturing or securing the post 6 of the handle 3 to the jaws and vice versa (FIG. 2). The jaw members 8 and 9 brought together by the connector spring 10 allow pivoting of the jaw members about the post 6 of the handle 3.

Figure 3:
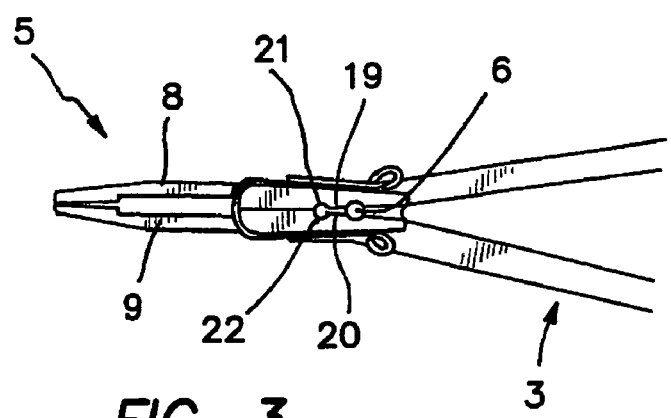
FIG. 3 illustrates a top view of one embodiment of the present invention of a disposable jaw being attached to a clip applier handle.
Figure 4:
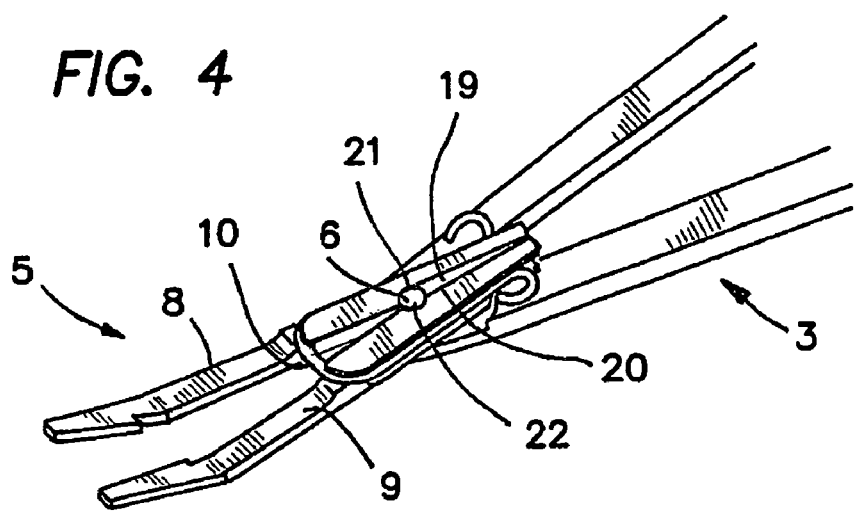
FIG. 4 illustrates a perspective view of one embodiment of the present invention of a clip applier and a clip.
Figure 5A:
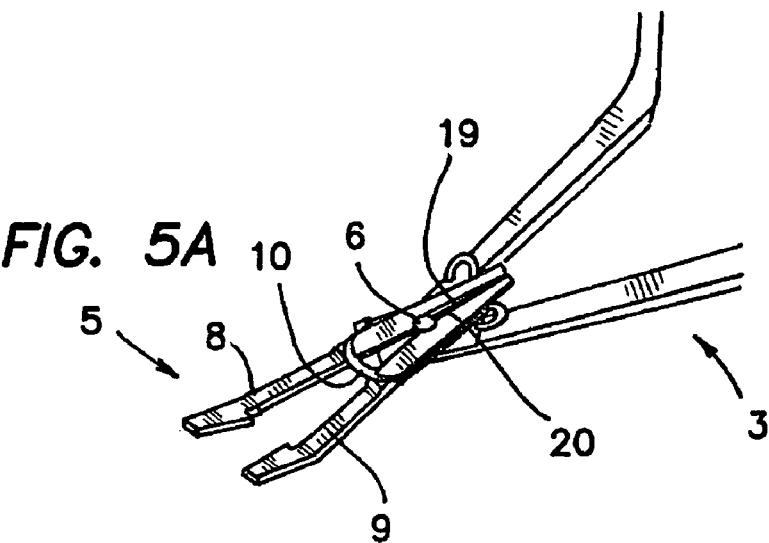
FIG. 5A illustrates a top view of one embodiment of the present invention of a clip applier handle and a disposable jaw overspread.

As such, as shown in FIG. 3, by pinching together the distal ends of the jaw members 8 and 9, the proximal ends of the jaw members 8, 9 spread apart. The post 6 may then be slid between the jaw members along, onto or over the shelves or channels 19, 20 and rest in the semi-hemispherical openings 21, 22. The post 6 serves as a hinge pin or point around which the two jaw members rotate. The post and/or corresponding opening in the jaw members may be spherical, cylindrical, rectangular or similarly shaped to provide pivotal engagement between the jaws and the handles. In another embodiment, the post or portions of the post extends from one or both of the jaw members and is received by corresponding opening in one or both of the handles. With the jaw members are released, the connector spring 10 biasing the proximal ends of the jaw members 8, 9 toward each other capture the post 6 within the semi-hemispherical openings 21, 22 (FIG. 4). The connector spring 10 and the curved proximal end of the semi-hemispherical opening prevents the post from being dislodged and thus the jaw members from being removed from the handles once the post is placed between the openings.

The integrity of the connection reduces any excessive play in this area, which may result in misalignment at the tips of the jaws, negatively affecting clip application. The connector spring 10 also provides stability in a vertical plane between the two jaw members 8, 9. It also forces the jaws to an open "at rest" state after the clip has been applied and pressure on the finger loops have been released. Furthermore, it provides a resisting force to excessive opening of the jaws, i.e., spreading the jaw tips wider than the "at rest" position, span A. "Overspreading", however, is incorporated into the jaws, e.g., the connector spring 10 is resilient or has resilient properties allowing overspreading, in one embodiment to facilitate clip retrieval as shown in FIGS. 5A-E. For example, in the process of retrieving a clip from its dispenser, the jaw tips slides over the full length of the clip until the clip is fully seated in the slots of the jaws. By allowing the jaws to "overspread" with some or mild tension, friction between clip and the jaws is reduced easing retrieval of the clip. Therefore, the jaws are allowed to spread sufficiently to slide slightly over the length of the clip but not excessively to complicate aligning or guiding of the clip applier to retrieve the clip. Also, tension provided by the connector spring 10 increases grasping or securing the clip between the jaws.

The proximal end of each jaw member 8, 9, in one embodiment, is serrated or include teeth, for example, one jaw member having projections, e.g., hills, and openings, e.g., valleys that mate with corresponding openings, e.g., valleys and projections, e.g., hills (longitudinally offset) in the other jaw member to increase stability and connection between the two jaw members 8, 9. In one embodiment, the distal end of one jaw member includes a bump or protrusion to be received by an aperture or opening in the distal end of the other jaw member which provides stability and alignment of the jaws during mounting of the jaws onto the handles. Jaw members 8,9 angled downward or upward to increase visibility of placement of the clips. Clip receiving portions angled inwardly to increase visibility retrieving and placing the clips between the jaws. Jaw members 8, 9 are spread slightly to receive post. In one aspect, the connector spring includes detents 27, 28, projections or protrusions extending laterally to be received by corresponding openings 29 in the jaw members or raised platforms to secure the connector spring 10 to the jaw members 8, 9 or raised platforms 15, 16.

Figure 6:
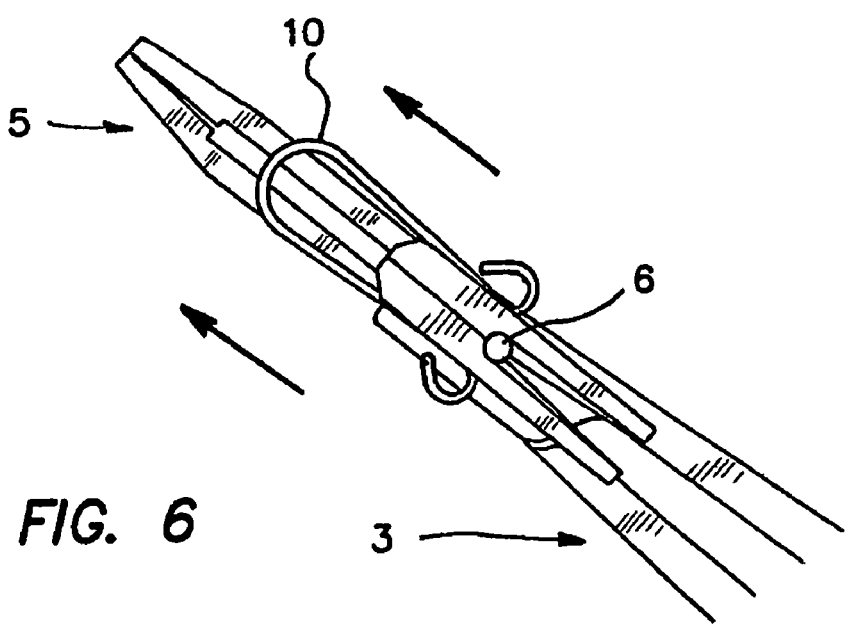
FIG. 6 illustrates a top view of one embodiment of the present invention of a disposable jaw being detached from a clip applier handle.
Figure 5B:
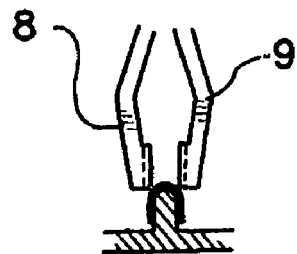
FIGS. 5B-E illustrate side views of one embodiment of the present invention of a clip applier handle and a disposable jaw overspread in relation to retrieving of a clip.
Figure 5C:
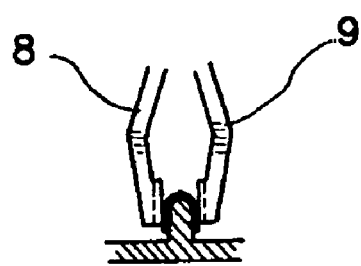
Figure 5D:
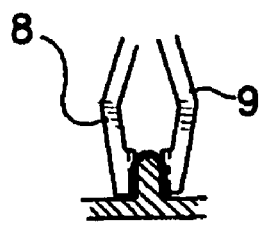
Figure 5E:
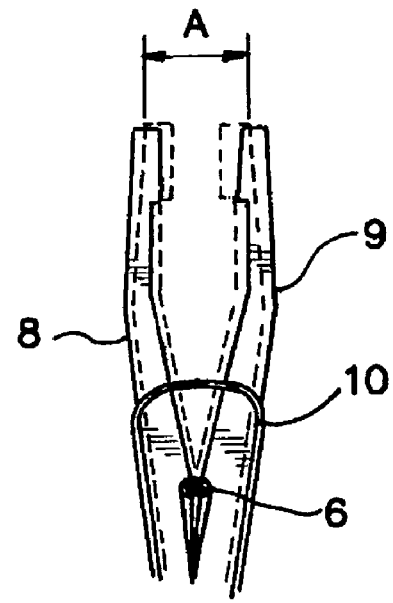

By removing the connector spring 10 from the jaw members 8, 9 to no longer couple or hold the jaw members 8, 9 together, e.g., sliding the connector spring 10 out of the slots 17, 18, the jaws may be disconnected from the handle (FIG. 6). As a result, the jaws become three distinct components, which may deter an attempt to re-use the jaws. In one embodiment, the connector spring 10 has loops, projections or extensions 23, 24 extending laterally from each leg of the connector spring 10. The loops 23,24 may be grasped or manipulated by fingers or other instruments assist in sliding the connector spring 10 out of engagement with the slot 17 and 18 of the jaw members 8, 9. In one embodiment, the connector spring 10 may be re-usable, though after multiple uses the connector spring 10 will likely become less resilient or unusable.

Figure 7A:
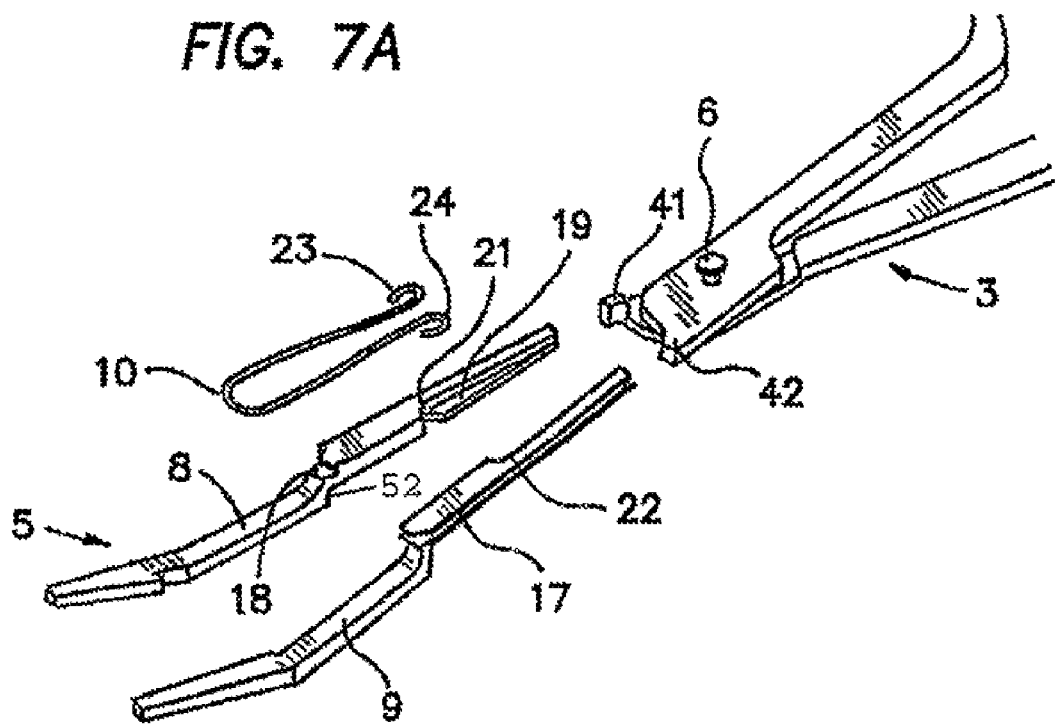
FIGS. 7A-B illustrate a perspective view of one embodiment of the present invention of a disposable jaw separated and a clip applier handle.
Figure 7B:
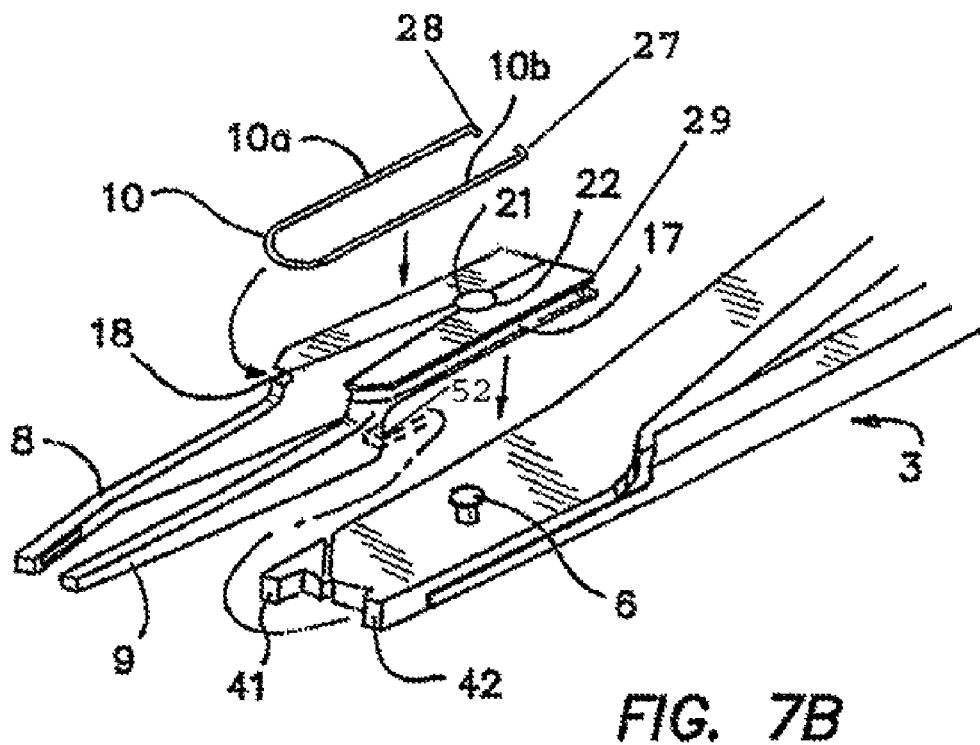

Stubs or projections 41, 42 extend from each handle for engaging a corresponding jaw member when the jaws are attached to the handles. In one embodiment, each jaw member has a corresponding cavity 52 or slot to mate or receive the projections 41, 42 extending from each handle. (FIG. 7A, 7B). The engagement of the projections 41, 42 with the corresponding jaw members 8, 9 causes the jaws to close when the handles are closed, e.g., squeezed together. With the handles released, the connector spring 10 forces open the jaws. Engagement of the projections 41, 42 with the corresponding jaw members 8, 9 causes the handles to open or spread apart. Likewise, when the handles are opened the jaws open and, in one embodiment, may be overspread.

As noted above, the detachable jaws allow for different size jaws to be attached to a common handle. Clips range in size from small to large in (commonly) five incremental steps. Each clip size may use its own set of corresponding jaws. As such, inventories of five different sizes of clip appliers, each of which takes up significant storage space, are typical. The clip applier's handle or the portion of the device from the pivot pin to the finger loops accounts for most of the space utilized. With the jaws being detachable, the re-usable handle may be utilized to accommodate all jaw sizes. As such, instead of carrying an inventory of numerous different sized clip appliers, inventories and thus also storage space may be reduced to one common handle and multiple sets or sized disposable jaws. The jaws are relatively small especially in relation to the handles and thereby utilize minimal storage space.

Figure 8A:
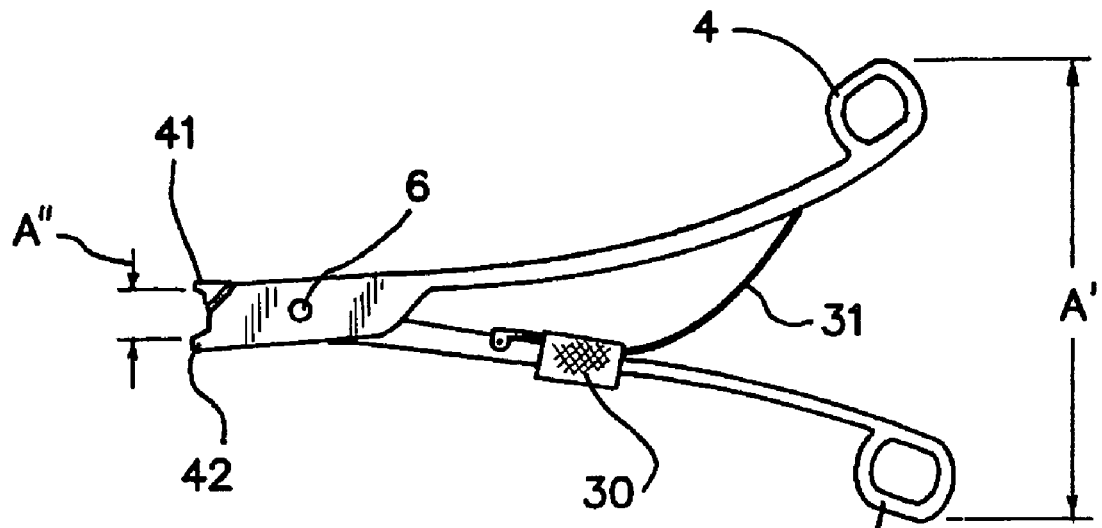
FIGS. 8A-B illustrate a top view of one embodiment of the present invention of a clip applier handle.
Figure 8B:
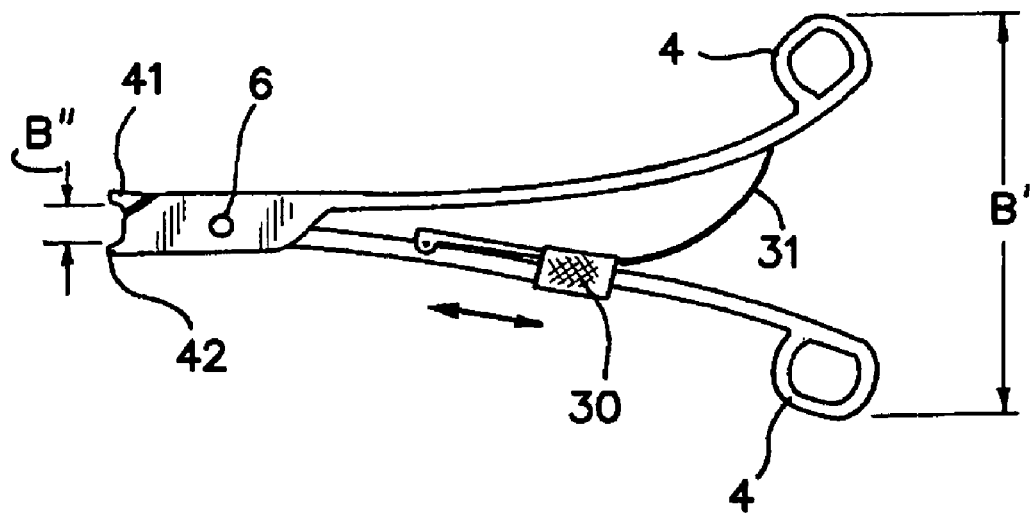

FIGS. 8A-B illustrate one embodiment of a common handle able to accommodate multiple jaw sizes. The movable connector, sleeve or slide 30 allows the spreading of the handle loops to be adjusted to multiple different dimensions that can be increased to accommodate larger sized jaws or decreased to accommodate smaller sized jaws. In each case, the slide 30 by changing the spacing between the handles ensures that when the handles are fully closed/opened the jaws are correspondingly closed/opened to fully crimp/release a clip between the jaws. Overspreading of the jaws is also permitted by properly dimensioning the spread or space between the handles by the slide 30.

As shown in FIGS. 8A-B, a leaf spring 31 is connected between the handles. One end of the leaf spring is secured one of the handles more distally than the other end of the leaf spring secured to the other handle. The slide 30 is coupled to the leaf spring 31 and one of the handles. The slide 30 moves or slides along the spring 31 and one of the handles. This adjusts the spacing or span between the finger loops of the handles, which correspondingly or proportionally adjusts the span at the distal end of the handles. For example, as shown in FIG. 8A, the larger the span between the finger loops, span A', the larger the sized jaws that may be accommodated, span A". Likewise, as shown for example in FIG. 8B, the smaller the span between the finger loops, span B', the smaller the sized jaws that may be accommodated, span B". In one aspect, the slide 30 moved in the distal direction or position causes a large span between finger loops and moved in the proximal direction or position causes a small span between finger loops. In one embodiment, the slide is incrementally connected to one of the handles to slide to different predetermined positions, e.g., five different positions pulling the spring 31 down, corresponding to different specific jaw sizes, e.g., five different jaw sizes. In one aspect, a ratchet mechanism is utilized with teeth on one of the handles and a corresponding pawl or tooth on the slide 30 or vice versa to govern the movement of the slide. In another aspect, a friction mechanism is utilized using, for example, a roller on the slide and corresponding grooves in one of the handles or vice versa governs the movement of the slide and thereby the accommodation and securing of different sized jaws on the common handle.

The jaws, in one embodiment, are electro-machined (EM) or metal injection molded (MIM) and discarded after each procedure. These processes allow rapid mass production of the jaws and assists in making the device economically feasible. In one embodiment, the jaw members, the connector spring or a combination thereof are disposable and in another embodiment, the jaws are disposable and the handles are re-usable or vice versa in another embodiment. The various embodiments described above where cavity and stubs or posts and openings, i.e., one connector type engaging or coupling to another connector type, are provided such components may be reversed. For example, stubs or projections may extend from the jaw members to interact with cavities within the handles to cause the jaws to operate in relation to the manipulation of the handles.

Accordingly, the present invention provides a single-fire clip applier with loadable jaws and methods thereof. Although this invention has been described in certain specific embodiments, many additional modifications and variations would be apparent to those skilled in the art. It is therefore to be understood that this invention may be practiced otherwise than specifically described, including various changes in the size, shape and materials, without departing from the scope and spirit of the present invention. Thus, embodiments of the present invention should be considered in all respects as illustrative and not restrictive, the scope of the present invention to be determined by the appended claims and their equivalents rather than the foregoing description.

The invention claimed is:

1. A surgical instrument for applying a surgical clip comprising:
   a disposable first jaw member having a proximal end, a distal end, and a first raised platform having a first slot extending generally longitudinally along an outer lateral surface of the first raised platform and a first channel extending generally longitudinally along an inner lateral surface of the first raised platform, the first channel including a first opening;
   a disposable second jaw member having a proximal end, a distal end, and a second raised platform having a second slot extending generally longitudinally along an outer lateral surface of the second raised platform and a second channel extending generally longitudinally along an inner lateral surface of the second raised platform, the second channel including a second opening; and
   a connector spring releasably mounted to the first and second raised platform and having a first leg and a second leg, the first leg slidably coupled to the slot of the first raised platform and the second leg slidably coupled to the slot of the second raised platform, the connector spring biasing the proximal end of the first and second jaw members together and the distal end of the first and second jaw members apart, and wherein the first and second openings are arranged to receive a post extending from a handle about which the first and second jaw members are rotatable with respect to one another.

2. The instrument of claim 1 wherein:
   the connector spring further comprises a bight;
   the first raised platform further comprises a proximal end and a distal end and the first slot of the first raised platform extends further generally laterally along the proximal end of the first raised platform and a portion of the bight of the connector spring is operationally engaged to the first slot of the first raised platform; and
   the second raised platform further comprises a proximal end and a distal end and the second slot of the second raised platform extends further generally laterally along the proximal end of the second raised platform and another portion of the bight of the connector spring is operationally engaged to the second slot of the second raised platform.

3. The instrument of claim 1 wherein the connector spring has resilient properties biasing the distal end of the first and second jaw members apart in an at rest state and permitting the distal end of the first and second jaw members to move further apart than their position in the at rest state.

4. The instrument of claim 1 wherein the connector spring further comprises a first projection extending laterally away from the first leg and a second projection extending laterally away from the second leg.

5. The instrument of claim 1, wherein the first channel extends from the proximal end of the first jaw member and is tapered on one end and has the first opening on the other end and the second channel extends from the proximal end of the second jaw member and is tapered on one end and has the second opening on the other end.

6. The instrument of claim 1 further comprising:
   a cavity disposed in the first jaw member near the distal end of the first raised platform;
   a stub extending from a first handle portion for engaging the cavity disposed in the first jaw member;
   a cavity disposed in the second jaw member near the distal end of the second raised platform; and
   a stub extending from a second handle portion for engaging the cavity disposed in the second jaw member.

7. The instrument of claim 1 wherein the first jaw member further comprises a clip receiver having a slot and positioned near the distal end of the first jaw member and the second jaw member further comprises a clip receiver having a slot and positioned near the distal end of the second jaw member.

8. The instrument of claim 1 wherein the handle further comprising:
   a first handle portion;
   a second handle portion coupled to the first handle portion; and
   an adjustable slide and leaf spring with one end of the leaf spring connected to one of the first and second handle portions and the other end of the leaf spring connected to the other one of the first and second handle portions, the slide connected to the leaf spring and one of the first and second handle portions.

9. The instrument of claim 8, wherein the disposable first jaw member, the disposable second jaw member, and the connector spring define a first jaw assembly removably attachable to the first handle portion and the second handle portion, and further comprising a second jaw assembly removably attachable to the first handle portion and the second handle portion.

10. The instrument of claim 9, wherein the first jaw assembly is a different size than the second jaw assembly.

11. The instrument of claim 1 wherein the first raised platform includes an aperture arranged to receive a detent on the first leg of the connector spring and the second raised platform includes an aperture arranged to receive a detent on the second leg of the connector spring such that when the detents of the connector spring are received in the corresponding apertures, the connector spring is secured to the first and second jaw members.

12. The instrument of claim 1 wherein the handle further comprising:
   a first handle portion;
   a second handle portion; and
   means for connecting the first and second handle portions to the first and second jaw members.

13. The instrument of claim 12 further comprising means for adjusting separation between the first and second handle.

14. The instrument of claim 1, wherein the first raised platform extends longitudinally from about a midpoint of the first jaw member to the proximal end of the first jaw member, and the second raised platform extends longitudinally from about a midpoint of the second jaw member to the proximal end of the second jaw member.

15. A surgical instrument for applying a surgical clip comprising:
   a disposable first jaw member having a proximal end, a distal end, and a first raised platform having a first slot extending lengthwise along the first raised platform;
   a disposable second jaw member having a proximal end, a distal end, and a second raised platform having a second slot extending lengthwise along the second raised platform;
   a connector spring releasably mounted to the first and second raised platform and having a first leg and a second leg, the first leg slidably coupled to the slot of the first raised platform and the second leg slidably coupled to the slot of the second raised platform, the connector spring biasing the proximal end of the first and second jaw members together and the distal end of the first and second jaw members apart;

a first channel extending from the proximal end of the first jaw member tapered on one end and having an opening on the other end; and a second channel extending from the proximal end of the second jaw member tapered on one end and having an opening on the other end, wherein the openings of the first and second channels are arranged to receive a post extending from a handle about which the first and second jaw members are rotatable with respect to one another.

16. The instrument of claim 15 further comprising:

a cavity disposed in the first jaw member near the distal end of the first raised platform;

a stub extending from a first handle portion for engaging the cavity disposed in the first jaw member;

a cavity disposed in the second jaw member near the distal end of the second raised platform; and a stub extending from a second handle portion for engaging the cavity disposed in the second jaw member.

* * * * *